United States Patent [19]

Parsons et al.

[11] Patent Number: 4,873,235
[45] Date of Patent: Oct. 10, 1989

[54] BENZOFUSED LACTAMS AS ANTIHYPERTENSIVES

[75] Inventors: William H. Parsons, Avenel; Arthur A. Patchett, Westfield; Eugene D. Thorsett, Fanwood, all of N.J.

[73] Assignee: Merck & Co., Inc., Rahway, N.J.

[21] Appl. No.: 473,792

[22] Filed: Mar. 16, 1983

Related U.S. Application Data

[63] Continuation-in-part of Ser. No. 383,435, Jun. 1, 1982, abandoned.

[51] Int. Cl.$^4$ ..................... A61K 31/47; C07D 217/24
[52] U.S. Cl. .................................. 514/312; 514/183; 540/463; 540/503; 546/157
[58] Field of Search ................. 260/239.3 B; 546/158, 546/138; 424/244, 258; 540/461, 463, 523, 527; 314/213, 312, 183

[56] References Cited

U.S. PATENT DOCUMENTS 4,410,520 10/1983 Watthey ........................ 260/239.3 B
4,470,988 9/1984 Watthey ........................ 260/239.3 B Primary Examiner—Robert T. Bond
Attorney, Agent, or Firm—Salvatore C. Mitri; Joseph F. DiPrima

[57] ABSTRACT

Benzofused lactams of the formula:

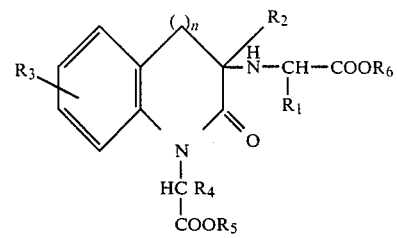

and their use as angiotensin converting enzyme inhibitors and antihypertensive agents are disclosed.

18 Claims, No Drawings

BENZOFUSED LACTAMS AS ANTIHYPERTENSIVES

This application is a continuation-in-part of application Ser. No. 383,435 filed June 1, 1982, now abandoned.

BACKGROUND OF THE INVENTION

The invention is concerned with benzofused lactams having angiotensin converting enzyme (ACE) inhibiting and antihypertensive activity.

Non-benzofused lactams having ACE inhibiting and antihypertensive activity are disclosed in EPO 046,291, EPO 046,289 and EPO 046,292.

Benzofused lactams having ACE inhibiting and antihypertensive activities have been discovered.

SUMMARY OF THE INVENTION

Benzofused lactams having the formula

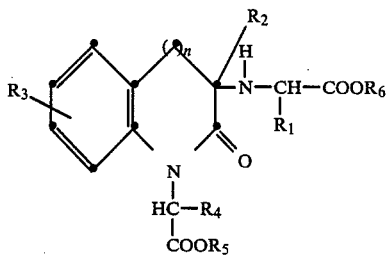

and their pharmaceutical use.

DETAILED DESCRIPTION OF THE INVENTION

An embodiment of the invention is a class of compounds having the formula:

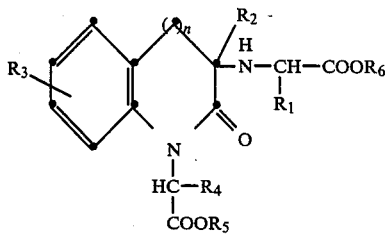

and pharmaceutically acceptable salts thereof wherein n is 1, 2 or 3, $R_4$ is hydrogen, lower alkyl, phenyl, phenyl lower alkyl, hydroxy phenyl lower alkyl, hydroxy lower alkyl, amino lower alkyl, acylamino lower alkyl, guanidino lower alkyl, imidazolyl lower alkyl, indolyl lower alkyl, mercapto lower alkyl or lower alkyl thio lower alkyl;

$R_2$ is hydrogen, $R_3$ is H, halo, lower alkyl, lowercycloalkyl, or loweralkoxy, $R_1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8-12 carbon atoms; aryl or heteroaryl which may be mono-, dior trisubstituted by loweralkyl, hydroxy, loweralkoxy, halo, amino, acylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, dior tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n$—Q—$(CH_2)_m$ wherein n is 0-2, m is 1-3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R_5$ and $R_6$ are independently selected from H, lower alkyl, lower alkenyl, diloweralkylamino, loweralkyl, substituted lower alkyl wherein the substituents are monohydroxy, dihydroxy or acylamino; acylloweralkyl and arloweralkyl; and, the pharmaceutically acceptable salts thereof.

Pharmaceutically acceptable salts are salts of Formula I with various inorganic and organic acids and bases. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like, also salts with organic and inorganic acids such as HCl, HBr, $H_2SO_4$, $H_3PO_4$, methanesulfonic, oxalic, pamoic, isethionic, toluenesulfonic, maleic, fumaric, camphorsulfonic, acetic or pivalic acids and the like.

The salts may be prepared by conventional means, e.g., by reacting the free acid or free base forms of formula I with one or more equivalents of the appropriate base or acid in a suitable solvent or medium in which the salt is insoluble or in a solvent or medium in which the salt is insoluble, or in a solvent such as water which is then removed in vacuo or by freeze-drying or by exchanging the ions of an existing salt for another ion on a suitable ion exchange resin.

The alkyl substituents recited above denote straight and branched chain hydrocarbons of $C_1$–$C_{12}$ such as methyl, hexyl, propyl, dodecyl isopentyl, isopropyl, nopentyl, etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon to carbon double bond or triple bond, respectively, such as vinyl, 2-butenyl and 1-hexynyl.

Cycloalkyl denotes rings composed of 5 to 8 methylene groups, each which may be substituted or unsubstituted with other hydrocarbon substituents, and include, for example, cyclopentyl, cycloheptyl, 4-methyl cyclohexyl, and the like. Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, for example, indolyl, quinolinyl, isoquinolinyl, benzimidazolyl, benzothiazolyl, benzthienyl, and naphthyridyl.

The acylamino substituent represents loweralkanoylamino and aroylamino. Preferred Formula I compounds are those where
n is 1, 2 or 3,
$R_5$ and $R_6$ are independently selected from hydrogen, lower alkyl, and arloweralkyl;
$R_2$ is hydrogen;
$R_1$ is alkyl of 1–10 carbon atoms which include branched, cyclic and unsaturated alkyl groups; substituted loweralkyl wherein the substituent can be hydroxy, lower alkylthio, amino, alkylamino, lowerdialkylamino, and acylamino; substituted loweralkyl having the formula $R_A{}^1(CH_2)_n$—Q—$(CH_2)_m$— wherein n is 0–2, m is 1–3, $R_A{}^1$ is aryl or heteroaryl optionally substituted by alkyl, halo, dihalo, amino, cyano, hydroxy, or alkoxy, and Q is O, S, N—$R_B{}^1$, CONR$_C{}^1$, NR$_C{}^1$CO, or CH=CH wherein $R_B{}^1$ is hydrogen, loweralkyl, aralkyl, loweralkanoyl, or aroyl and $R_C{}^1$ is hydrogen or loweralkyl; aralkyl or heteroaralkyl which include branched loweralkyl groups; substituted aralkyl or substituted heteroaralkyl which include branched loweralkyl groups wherein the loweralkyl substituents can be amino, acylamino, or hydroxy and the aryl and heteroaryl substituents can be loweralkyl, halo, dihalo, amino, cyano, hydroxy, loweralkoxy, aminoloweralkyl, or hydroxyloweralkyl;
$R_4$ is hydrogen, lower alkyl, phenyl lower alkyl, hydroxy phenyl lower alkyl, amino lower alkyl, imidazolyl lower alkyl, indolyl lower alkyl, lower alkyl thio lower alkyl; and
$R_3$ is H, halo, lower alkyl, lowercycloalkyl, or lower alkoxy.

More preferred compounds of Formula I are those where
n is 1, 2 or 3,
$R_5$ and $R_6$ are independently selected from hydrogen, lower alkyl, and arloweralkyl;
$R_4$ is hydrogen, lower alkyl, amino lower alkyl, indolyl lower alkyl, phenyl lower alkyl;
$R_2$ is hydrogen;
$R_1$ is as defined above in the preferred group;
$R_3$ H, halo, lower alkyl or lower alkoxy.

Most preferred compounds of Formula I are those where
n is 1, 2 or 3,
$R_4$ is hydrogen, or lower alkyl;
$R_1$ is as defined above in the preferred group;
$R_2$ is hydrogen,
$R_5$ and $R_6$ are independently selected from hydrogen, lower alkyl, and benzyl; and
$R_3$ is H, halo, lower alkyl or lower alkoxy.

A preferred value of n in the above described subgenera is 3 or 2, and more preferably 2.

The preferred, more preferred and most preferred compounds of Formula I also include the pharmaceutically acceptable salts thereof.

The pharmaceutically acceptable salts are salts of Formula I compounds with various inorganic and organic acids and bases. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like, and salts with organic and inorganic acids; e.g., HCl, HBr, $H_2SO_4$, $H_3PO_4$, methanesulfonic, isethionic, pivalic, oxalic, toluenesulfonic, maleic, fumaric, camphorsulfonic acids and the like.

The salts may be prepared by conventional means, e.g., reacting the free acid or free base form of the product with one or more equivalents of the appropriate base or acid in an appropriate solvent or reaction medium.

The compounds of formula I inhibit angiotensin converting enzyme and thus block conversion of the decapeptide angiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with reno-vascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys.. Acta,* 206 136 (136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 125, 96 (1967).

Thus, the present Formula I compounds are useful in treating hypertension. They are also of value in the management of acute and chronic congestive heart failure, in the treatment of secondary hyperaldosteronism, scleroderma, primary and secondary pulmonary hypertension, renal failure and renal vascular hypertension, and in the management of vascular disorders such as migraine. The application of the compounds of this invention for these and similar disorders will be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 200 mg. per patient per day which can be administered in single or multiple doses. Preferably, the dosage range will be about 2.5 to 100 mg. per patient per day.

It is often advantageous to administer compounds of this invention in combination with other antihypertensives and/or diuretics. For example, the compounds of this invention can be given in combination with such compounds as amiloride, atenolol, benzofluoromethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivalogloxyethyl ester of methyldopa, indacrinone and variable ratios of its enantiomers, nifedipine, verapamil, diltiazem, fluoroethiazide, atenolol, (+)-4-{3-{-[2-(1-hydroxycyclohexyl) ethyl]-4-oxo-2-thiazolidinyl}propyl}benzoic acid, bumetanide, prazosin, propranolol, *rauwolfia serpentina,* rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5-100 milligrams per day range can be effectively combined at levels at the 0.5-100 milligrams per day range with the following compounds at the indicated per day dose range: hydrochlorothiazide (10-100 mg), timolol (5-6) mg), methyl dopa (65-2000 mg), the pivaloyloxyethyl ester of methyl dopa (30-1000 mg), indacrinone and variable ratios of its enantiomers (25-150 mg) and (+)-4-{3-{[2-(1-hydroxycyclohexyl)ethyl]-4-oxo-2-thiazolidinyl}propyl}-benzoic acid (10-100 mg).

In addition, the triple drug combinations of hydrochlorothiazide (10-100 mg) plus timolol (5-60 mg) plus converting enzyme inhibitor of this invention (0.5-100 mg) or hydrochlorothiazide (10-100 mg) plus amiloride (5-20 mg) plus converting enzyme inhibitor of this invention (0.5-100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 0.5 to 100 mg of a compound or mixture of compound of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The compounds of Formula I may be prepared by any convenient process. Useful processes are illustrated by the following reaction equations.

Process A

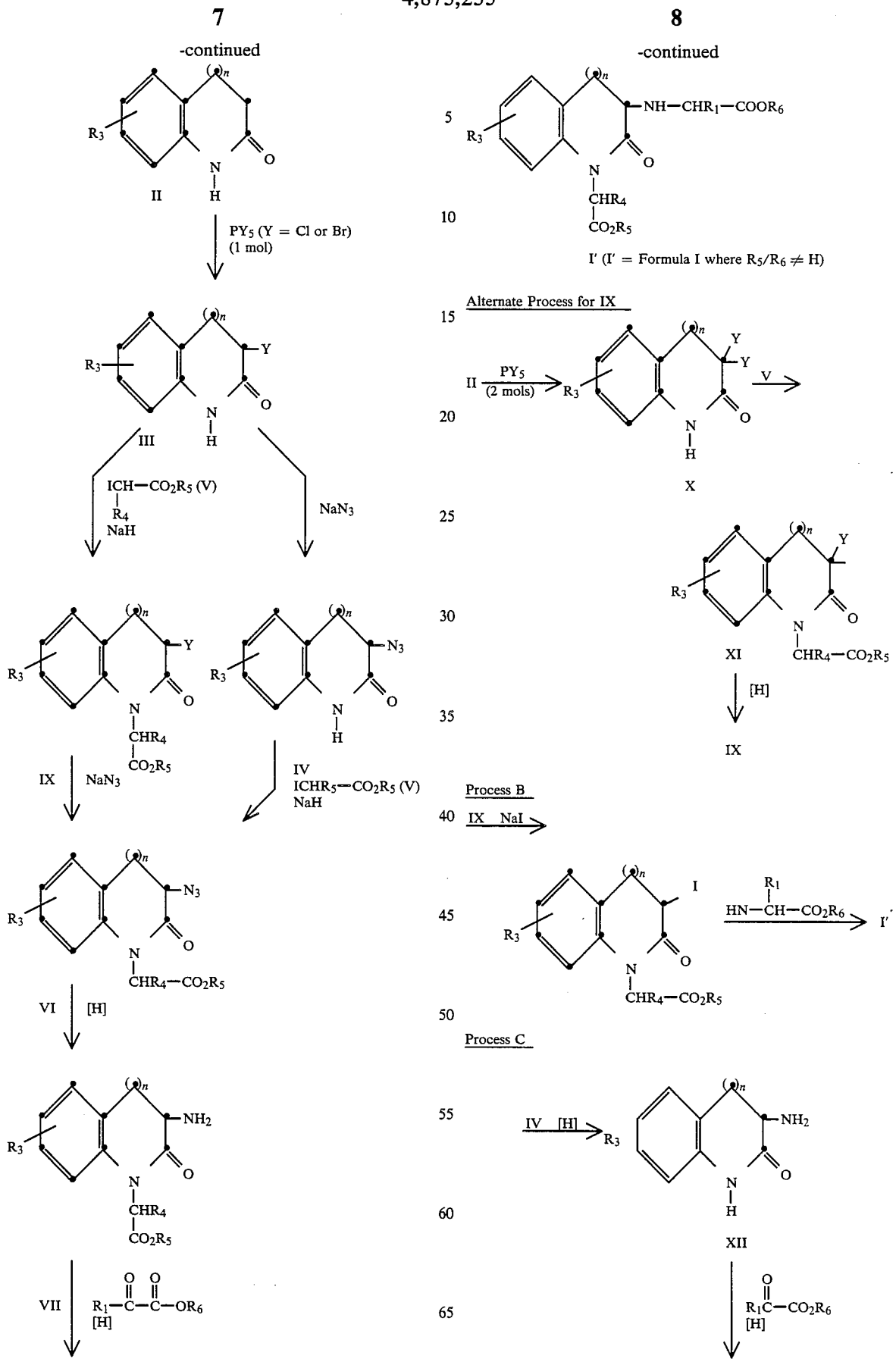

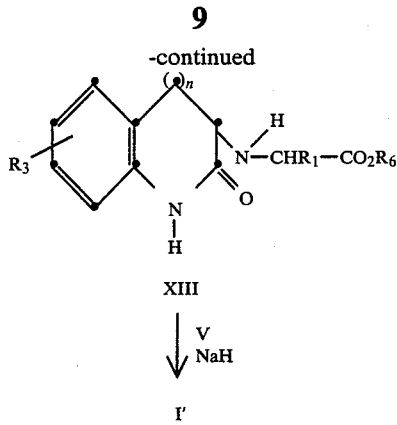

XIII

↓ V
↓ NaH

I′

Process A

Benzofused lactam II ring size ranging from 6 to 8 (n=1, 2, 3), prepared from a precursor ketone by a procedure of Blicke et al., *J. Am. Chem. Soc.*, 76, 2317 (1954), is converted to (III), with PX$_5$ where X=Br or Cl [Nagasawa et al., *J. Med. Chem.*, 14, 501(1971)]. Reaction of (III) with sodium or lithium azide in a suitable solvent such as DMF or ethanol [see, for example, Brenner et al., *Helv. Chem. Acta*, 41, 181 (1958)] affords (IV) which can be alkylated with an iodoester (V) in the presence of a strong base, like sodium hydride, in a solvent such as DMF or THF to produce (VI). Reduction of (VI) with hydrogen and a suitable catalyst, such as palladium on carbon, affords (VII). Intermediate (VII) is then reductively coupled with a keto acid or ester (VIII) in a solvent such as ethanol using a catalyst such as palladium on carbon to afford (I′) (R$_5$ and R$_6$ ≠H). Alternatively, sodium cyanoborohydride can be used to effect the reduction.

Groups R$_5$ and R$_6$ may be modified by known methods, if desired. For example, if R$_5$=Et and R$_6$=t-Bu, the diester (I) can be converted to the monoester R$_5$=Et and R$_6$=H by treatment with trifluoroacetic acid. If R$_5$=R$_6$=Et, (I) can be converted to the diacid R$_5$=R$_6$=H by basic hydrolysis.

Alternatively, (III) may be alkylated with (V) in the presence of a strong base, like sodium hydride, and the intermediate (IX) converted to (VI) by reaction with an azide salt as described above.

Alternate Process for IX

If desired, (IX) may be prepared by the alkylation of (X) [prepared from II using the alternate conditions of Nagasawa, above] with (V) to afford intermediate (XI). Treatment of (XI) with hydrogen and a catalyst, such as palladium on carbon, affords (IX).

Process B

Alternatively, IX (Y=Cl, Br; R$_5$≠H) may be converted to the iodo compound IX (X=I) by known methods, for example, sodium iodide in acetone. Reaction of this iodo lactam with an amino acid ester in a solvent such as toluene or DMF in the presence of a halide scavenger such as Ag$_2$O gives I (R$_6$≠H, R$_5$≠H).

PROCESS C

If desired, IV may be reduced with hydrogen in the presence of a suitable catalyst to afford XII which can be alkylated with a ketoester in the presence of hydrogen on a suitable catalyst to give XIII. Alternatively, sodium cyanoborohydride may be used. Alkylation of XIII to afford I′ (R$_6$≠H, R$_5$≠H) can be carried out with an iodoester in the presence of a strong base such as sodium hydride in a solvent such as THF.

In the compound of Formula I, the carbon atoms to which R$_1$, R$_2$ and R$_4$ are attached and the ring carbon atom to which the

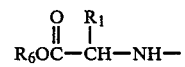

group is attached may be asymmetric. Thus, the compounds of this invention exist in diastereoisomeric forms or in mixtures thereof. The processes described above can utilize racemates, enantiomers or diastereomers as starting materials. When diastereomeric intermediates or products result from the synthetic procedures, the diastereomeric intermediates or products can be separated by chromatographic or fractional crystallization methods. When racemic mixtures result, they may be resolved by crystallization of salts of optically active acids or bases or by other methods known in the art. The part-structures

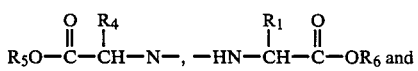

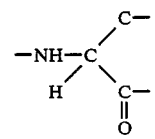

of Formula I can be in two configurations (S or R) and both are within the scope of this invention, although S is generally preferred. Both configurations at the carbon to which R$_2$ is attached are encompassed within this invention.

The following Examples illustrate preparation of representative compounds of Formula I. All temperatures are in °C.

EXAMPLE 1

A. t-Butoxycarbonylmethyl-3-aminodihydrocarbostyril

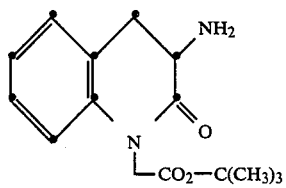

To a suspension of 2.42 gm NaH (50% oil dispersion washed 3 ×hexanes) in 50 ml of THF at 0° C. was added solid 5 gm (0.025 mol) of 3-aminodihydrocarbostyrilhydrochloride (T. J. McCord, Arch. of Biochem. & Biophys. 102 48 (1963)) stirring at 0° C. until the evolution of hydrogen had ceased at which time the reaction mixture was warmed to room temperature and stirred a further 1 hour. To the stirred reaction mixture was added dropwise a solution of 6 gm of t-butyl iodoacetate in 20 ml of THF stirring a further 2 hours at room temperature at which time the reaction was quenched with 20 ml of saturated NaHCO$_3$. The reaction mixture was diluted with 20 ml of H₂O and extracted 2×50 ml of 9:1 ethylacetate:acetonitrile. The organic layers were combined, filtered through MgSO₄ and concentrated in vacuo to give 5 gm of 1-t-butoxycarbonylmethyl-3-aminodihydrocarbostyril. NMR (CDCl₃, TMS) 1.4 (s, 9H); 2.0-3.2 (m, 4H), 3.4-3.8 (m, 1H); 4.6 (Q, 2H); 6.6-7.2 (m, 4H) IR C═O 1738, 1680

B.
1-Carbomethoxymethyl-3-(1-carboethoxy-3-phenyl-1-propyl)aminodihydrocarbostyril (racemate mixture)

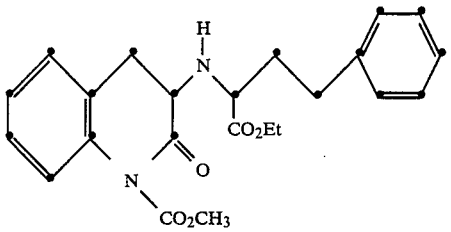

A solution of 2.76 gm (0.010 mol) of 1-t-butoxycarbonylmethyl-3-amino dihydrocarbostyril, 10 gm of ethyl 4-phenyl-2-oxo-butyrate and 0.60 ml of acetic acid in 20 ml of absolute ethanol was stirred 1 hour at room temperature at which time was added dropwise over 8 hours a solution of 1.57 gm of NaCNBH₃ in 20 ml of ethanol. After stirring a further 4 hours at room temperature the reaction mixture was concentrated in vacuo. The crude reaction mixture was partitioned between H₂O and ethylacetate. The aqueous layer was extracted 2× with ethylacetate and the combined organic layers filtered through MgSO₄ and concentrated at reduced pressure. The reaction mixture was diluted with 20 ml of trifluoroacetic acid and stirred 2 hours at room temperature after which it was concentrated at reduced pressure. The crude mono acid (B where CH₃ is H) was taken up in 20 ml of saturated NaHCO₃, washed 3×50 ml of ethyl acetate. The aqueous layer was concentrated in vacuo, redissolved in 30 ml of methanol, cooled to 0° C., saturated with HCl gas, sealed, warmed to room temperature and stirred overnight at room temperature. The reaction mixture was subsequently concentrated in vacuo, diluted with saturated K₂CO₃ and extracted 3 times with ethyl acetate. The combined organic fractions were filtered through MgSO₄ and concentrated at reduced pressure. The crude reaction product B was chromatographed (silica, 2:1 ether:hexanes) and two diastereomeric B racemates were isolated. Racemate A 500 mg TLC (silica, 2:1 ether:hexanes) R$_f$=0.28

NMR (CDCl₃, TMS) 1.2 (t, 3H); 1.8-2.2 (m, 3H); 2.6-3.1 (m, 6H); 3.2-3.6 (m, 2H); 3.65 (s, 3H); 4.1 (Q, 2H); 4.6 (Q, 2H); 6.8-7.1 (s, 9H)

Racemate B 1.5 gm

TLC (silica, 2:1 ether:hexanes) R$_f$=0.20

NMR (CDCl₃, TMS) 1.3 (s, 3H); 1.8-3.2 (m, 8H); 3.4-3.7 (m, 2H); 3.7 (s, 3H); 4.1 (Q, 2H); 4.6 (Q, 2H); 6.8-7.2 (m, 9H).

EXAMPLE 2

1-Carboxymethyl-3-(1-carboxy-3-phenyl-1-propyl)-dihydrocarbostyril

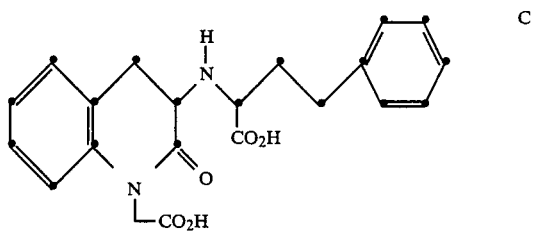

Racemate A

A reaction mixture consisting of 900 mg (0.00212 mol) of the diester racemate A of Example 1, 2 ml of methanol and 2.2 ml of a 4N solution of NaOH in H₂O was stirred 12 hours at room temperature. Subsequently the reaction mixture was concentrated at reduced pressure. Upon acidification with acetic acid the diacid C precipitated out and was filtered, washed with H₂O and dried, giving 600 mg of the diacid C as its mono sodium salt.

TLC (silica, 1:1:1:.5 H₂O:nB₄OH:EtOAc:HOAc) R$_f$ 0.50

An. Calc. for C₂₁H₂₂N₂O₅Na. 1.5 H₂O C, 58.27; H, 5.43; N, 6.47. Found: C, 58.11; H, 5.62; N, 6.02

EXAMPLE 3

A. 3-Bromo-homodihydrocarbostyril

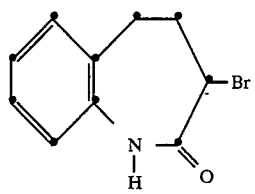

To a solution of 15 gm (0.093 mol) of homo dihydrocarbostyril (L. H. Briggs, J.C.S., 456 (1937)) in 200 ml of chloroform was added in increments over a period of an hour 19 gm of PCl₅ at which time was added 140 mg of iodine followed by a slow dropwise addition of 90 ml of a 1M solution of bromine in chloroform. The reaction mixture was warmed to room temperature where stirring was continued a further 1 hour.

The crude reaction mixture was concentrated in vacuo and then partitioned between water, ice and chloroform. The aqueous layer was extracted 2 times with methylene chloride and the combined organic fractions were filtered through MgSO₄ and concentrated in vacuo. The crude bromide D was chromatographed (silica, 2:1 ether:hexanes) to give 6.5 gm of pure D bromide.

TLC (silica, 2:1 ether:hexanes) R$_f$=0.65

NMR (CDCl₃, TMS) 2.4-3.0 (m, 4H); 4.4-4.7 t, 1H); 7.2 (s, 4H); 9.2 (bs, 1H)

IR 1650 cm⁻¹.

mass spectrum: M+239, m/e: 241 (M+, +2); 160 (M+² —Br); 132 (—C═O).

B. 3-Azido homodihydrocarbostyril

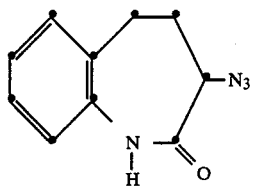

E

To a solution of 9.98 gm (0.0417 mol) of 3-bromo homodihydrocarbostyril in 200 ml of DMF was added 10.8 gm of sodium azide stirring 12 hours at 60° C. at which time the DMF was removed at reduced pressure. To the crude reaction mixture was added 50 ml of water and the mixture was then extracted 3 times with 50 ml of chloroform. The combined organic fractions were combined, washed with 25 ml of a saturated solution of NaCl, filtered through MgSO$_4$ and concentrated at reduced pressure. Chromatography (silica, 2:1 ether:-hexanes) gave 7.92 gm of pure E azide. m.p. 150°–151° C.

TLC (silica, 2:1 ether:hexanes) R$_f$=0.71

El. An. Calc. for C$_{10}$H$_{10}$N$_4$O  N, 27.71; C, 59.39; H, 4.98

Found N, 27.27; C, 59.25; H, 4.98

NMR (CDCl$_3$, TMS) 2.2–2.8 (m, 4H), 3.6–4.0 (dd, 1H); 7.2 (bs, 4H) 9.2 (bs, 1H) IR N$_3$ 2130, CO 1678 mass spectrum: M$^+$202, m/e 174 (M$^+$-N$_2$; 146 (C=O)

C. 1-t-Butoxycarbonylmethyl-3-azido homodihydrocarbostyril

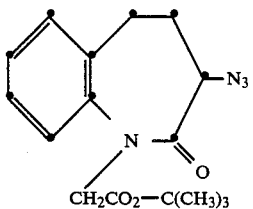

F

To a suspension of 1 gm of sodium hydride (50% dispersion in oil washed 3 times with hexanes) in 20 ml of THF at 0° C. was added dropwise a solution of 4.2 gm (0.02 mol) of 3-azido homodihydro carbostyril and 3 ml of t-butyl iodo acetate in 20 ml of THF. The reaction was carefully monitored by TLC (silica, 2:1 ether:hexanes) until reaction was complete at which time the reaction was quenched with 30 ml of saturated NH$_4$Cl, diluted with 20 ml H$_2$O and extracted 3 times with 50 ml CH$_2$Cl$_2$. The combined organic layers were filtered, concentrated in vacuo and chromatographed (silica, 2:1 ether:hexanes) to give 4.5 gm of pure product F.

m.p. 103°–104° C.

TLC (silica, 211 ether:hexanes) R$_f$=0.74

El. An. Calc. for C$_{16}$H$_{20}$N$_4$O$_3$N, 17.71; C, 60.74; H, 6.37 Found N, 17.39; C, 60.54; H, 6.61

NMR (CDCl$_3$, TMS) 1.5 (s, 9H), 2.2–3.4 (m, 4H); 3.5–4.0 (overlapping doublets, 1H); 4.2–4.8 (ABQ, 2H); 7.2 (s, 4H)

mass spectrum: M$^+$ 316, m/e 288 (M$^+$—N$_2$; 260 (M$^+$—C$_4$H$_9$)

D. 1-t-Butoxycarbonylmethyl-3-amino homodihydrocarbostyril

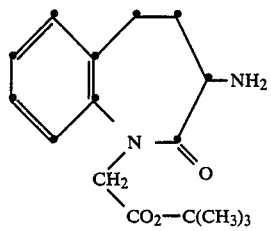

G

A solution of 8.01 gm of 1-t-butoxycarbonylmethyl-3-azido homo dihydrocarbostyril in 150 ml of absolute ethanol with 0.8 gm of Pd/C 10% was hydrogenated for 12 hr at room temperature and 40 lbs of H$_2$. The reaction was subsequently filtered and the ethanol removed at reduced pressure to give 7.05 gm of pure amine G. m.p. 107°–109° C.

El. An. Calc. for C$_{16}$H$_{22}$N$_2$O$_3$.$\frac{1}{4}$H$_2$O  N, 9.36; C, 64.19; H, 7.41 Found N, 9.18; C, 64.17; H, 7.53

NMR (D$_2$O, CDCl$_3$, TMS) 1.4 (s, 9H), 2.2–3.8 (m, 5H); 4.1–4.7 (ABQ, 2H); 7.05 (bs, 4H)

IR C=O 1735, 1660 mass spectrum: M$^+$ 290, m/e 262 (M$^+$-C=O); 234 (M$^+$-C$_4$H$_8$); 217 (M$^+$-C$_4$H$_9$O).

E. 1-t-Butoxycarbonylmethyl-3-(1-carboethoxy-3-phenyl-1-propyl)-amino homodihydrocarbostyril (Racemate mixture)

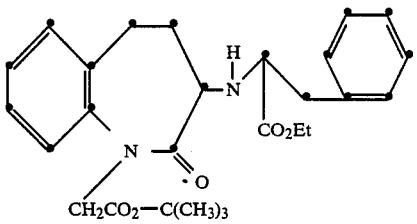

H

A solution of 1 gm (0.00345 mol) of 1-t-butoxy carbonylmethyl-3-amino homodihydrocarbostyril, 3.5 gm of ethyl 4-phenyl-2-oxobutyrate and 200 μl of acetic acid in 12 ml of absolute ethanol was stirred 1 hour at room temperature. To the stirred solution was added dropwise over a 12 hour period a solution of 545 mg of NaCNBH$_3$ in 12 ml of ethanol. After stirring a further 8 hours the reaction was concentrated at reduced pressure and partitioned between H$_2$O and ethyl acetate. After extracting twice with ethyl acetate the combined organic layers were filtered through MgSO$_4$ and concentrated in vacuo. The crude reaction mixture was chromatographed (silica, 1:1 ether:hexanes) and two diastereomeric H racemates were isolated.

Racemate Diester A 450 mg

TLC (silica, 1:1, ether:hexanes) R$_f$=0.31

NMR (CDCl$_3$, TMS) 1.1–1.4 (t, 3H), 1.45 (s, 9H); 1.8–3.2 (m, 11H); 3.9–4.3 (Q, 2H); 4.1–4.7 (ABQ, 2H); 7.1–7.3 (m, 9H)

Racemate Diester B 520 mg

TLC (silica, 1:1, ether:hexanes) R$_f$=0.23

NMR (CDCl$_3$, TMS) 0.9–1.2 (t, 3H), 1.4 (s, 9H); 1.8–3.4 (m, 11H); 3.8–4.2 (Q, 2H); 4.1–4.7 (ABQ, 2H); 7.2 (s, 9H)

EXAMPLE 4

1-Carboxymethyl-3-(1-carboxy-3-phenyl-1-propyl)-aminohomodihydrocarbostyril

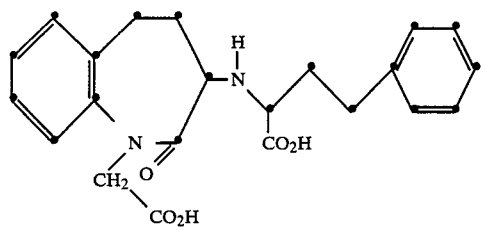

J

Racemate A 250 mg of racemate diester A of Example 3 was stirred 2 hours with 5 ml of trifluoroacetic acid at which time the reaction mixture was concentrated in vacuo. The crude product in 1 ml of H$_2$O was treated with 600 μl of a 4N NaOH in H$_2$O solution and stirred 7 hours at room temperature. The crude reaction mixture was partially concentrated in vacuo at which time the monosodium salt of J precipitated out. The suspension was filtered, the solid washed with H$_2$O and dried under vacuum to give 125 mg of a diacid monosodium salt of J.

TLC (silica, 1:1:1:.5, H$_2$O:ethylacetate:nBuOH:-HOAc)

R$_f$ 0.60,

El. An. Calc. for C$_{22}$H$_{23}$N$_2$O$_5$Na.2.5H$_2$O C, 56.90; H, 5.82; N, 6.04 Found C, 56.84; H, 5.64; N, 5.81

Racemate B 550 mg of the racemate diester B of Example 3 was converted to the diacid J by the same procedure described above to give 250 mg of free diacid.

TLC (silica, 1:1:1:.5, H$_2$O:ethylacetate:nBuOH:-HOAc)

R$_f$ 0.67

El. An. Calc. for C$_{22}$H$_{23}$N$_2$O$_5$.¼H$_2$O C, 66.02; H, 5.75; N, 7.00 Found C, 66.04; H, 6.13; N, 6.85

EXAMPLE 5

1-Carbomethoxymethyl-3-(1-carbomethoxy-3-phenyl-1-propyl)aminohomodihydrocarbostyril

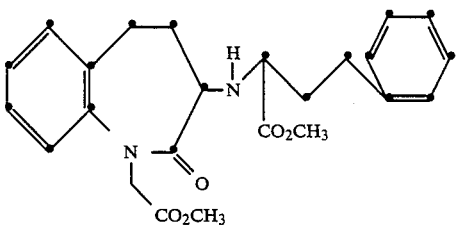

K

A solution of 1 gm of 1-carboxymethyl-3-(1-carboxy-3-phenyl-1-propyl)amino homodihydrocarbostyril (Racemate B of Example 4) in 20 ml of methanol was cooled to 0° C. and saturated with HCl gas. The reaction mixture was then sealed and stirred overnight at room temperature. The reaction mixture was subsequently concentrated at reduced pressure and partitioned between a saturated aqueous solution of K$_2$CO$_3$ and ethyl acetate. The aqueous layer was extracted two times with ethyl acetate and the combined organic fractions filtered through MgSO$_4$ and concentrated at reduced pressure. The crude product was chromatographed (silica, 3:1 ether:hexanes) to give 700 mg of pure dimethyl ester K.

TLC (silica, 3:1 ether:hexanes) R$_f$=0.56

An. Calc. for C$_{24}$H$_{28}$N$_2$O$_5$.¼H$_2$O N, 6.52; C, 67.13; H, 6.52 Found N, 6.28; C, 67.14; H, 6.60

NMR (CDCl$_3$, TMS) 1.8–3.4 (m, 11H); 3.5 (s, 3H); 3.7 (s, 3H); 4.2–4.7 (ABQ, 2H); 7.1 (bs, 9H)

EXAMPLE 6

1-Carboxymethyl-3-(1-carboethoxy-3-phenyl-propyl-)amino homodihydrocarbostyril

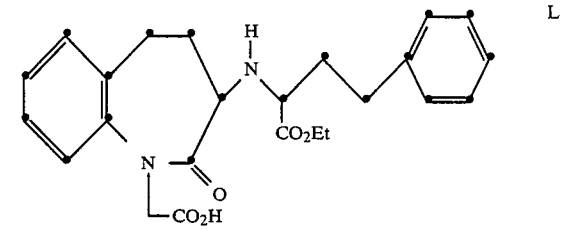

L

A solution of 550 mg of 1-t-butoxycarbonylmethyl-3-(1-carboethoxy-3-phenyl-1-propyl)amino homodihydrocarbostyril in 10 ml of trifluoroacetic acid was stirred at room temperature for 2 hours. The reaction mixture was concentrated in vacuo, diluted with water and concentrated a second time in vacuo to give a white solid. The solid was triturated with ether and filtered to give 400 mg of the CF$_3$CO$_2$H salt of the desired product L.

An. Calc. for C$_{24}$H$_{28}$N$_2$O$_5$.CF$_3$CO$_2$H H, 5.34; C, 57.51; N, 5.16 Found H, 5.46; C, 57.68; N, 5.03

NMR (CD$_3$OD) 1.2 (t, 3H); 2.0–3.0 (m, 9H); 3.6–4.2 (m, 4H); 4.5 (s, 2H); 7.1–7.3 (overlapping singlets, 9H).

EXAMPLE 7

1-Carbobenzyloxymethyl-3-(1-carboxy-3-phenyl-1-propyl)-amino homodihydrocarbostyril

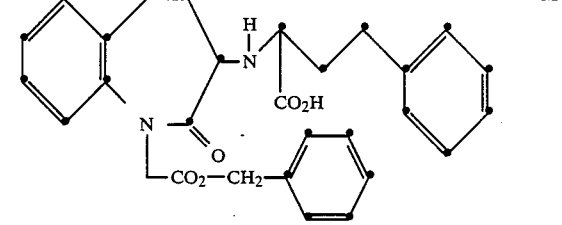

M

To a suspension of 1.90 gm of NaH (50% in oil washed 3 times with hexanes) in 40 ml of THF at room temperature was added dropwise a solution of 6.5 gm of 3-amino homodihydrocarbostyril and 1.56 gm of benzyliodoacetate in 10 ml of THF stirring a further 2 hr at room temperature. The reaction was subsequently quenched with 10 ml of H$_2$O and extracted two times with ethyl acetate. The combined organic fractions were filtered through MgSO$_4$ and concentrated in vacuo to obtain 1-carbobenzyloxymethyl-3-amino homodihydrocarbostyril.

NMR (CDCl$_3$, TMS) 1.8–3.0 (m, 6H); 3.1–3.4 (m, 1H); 4.6 (ABQ, 2H); 5.1 (s, 2H); 7.0–7.3 (m, 9H)

A solution of 5 gm of 1-carbobenzyloxymethyl-3-amino homodihydrocarbostyril, 16 gm of t-butyl-4-phenyl-2-oxobutyrate and 860 ml of acetic acid in 60 ml of absolute ethanol was stirred 1 hr at room temperature at which time was added dropwise over 18 hours a solution of 2.4 gm of NaCNBH$_3$ in 40 ml ethanol. The reaction mixture was concentrated in vacuo and partitioned between H$_2$O and ethyl acetate. The aqueous layer was extracted 2 times with ethyl acetate and the combined organic layers were filtered through MgSO$_4$ and concentrated in vacuo. The crude reaction mixture was chromatographed (silica 1:1 ether:hexanes) and the first diastereomeric racemate diester was isolated.

NMR (CDCl$_3$, TMS) 1.4 (s, 9H); 1.6–3.2 (m, 11H); 4.5 (ABQ, 2H); 4.6 (s, 2H); 7.0–7.3 (m, 14H)

Said diester in 5 ml of methylene chloride and 5 ml of trifluoro acetic acid was stirred 8 hr at room temperature at which time the reaction was concentrated in vacuo, redissolved in carbon tetrachloride and reconcentrated in vacuo to give 600 mg of monobenzyl ester M.

NMR (CDCl$_3$) 2.0–3.0 (m, 9H); 3.4–3.8 (m, 2H); 4.4 (bs, 2H); 5.0 (s, 2H); 7.0–7.3 (m, 14H)

EXAMPLE 8

A. 3-Bromohexahydrobenzoazocin-2-one

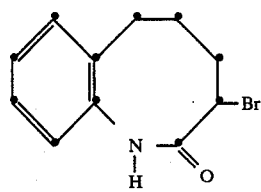

N

To a solution of 15 gm (0.084 mol) of hexahydrobenzoazocin-2-one (Chemica Scandinavia, 18, 191 (1964)) in 150 ml of chloroform at 0° C. was added 8.8 gm of PCl$_5$ in increments over a period of an hour. Subsequently, to the reaction mixture was added 70 mg of iodine followed by slow dropwise addition of 84 ml of a 1M solution of bromine in chloroform. The reaction mixture was warmed to room temperature and stirred for 1 hour at which time it was concentrated at reduced pressure. To the crude product was added a mixture of ice and water and the mixture was extracted 3 times with methylene chloride. The combined organic fractions were filtered through MgSO$_4$ and concentrated at reduced pressure. The solid bromide was recrystallized with a mixture of chloroform and hexanes to give 12 gm of pure product N.

m.p. 194°–195° C.

TLC (silica, 2:1 ether:hexanes) R$_f$=0.36

An. Calc. for C$_{11}$H$_{12}$NOBr.¼H$_2$O N, 5.41; C, 51.08; H, 4.68 Found N, 5.29; C, 50.75; H, 4.53

NMR (CDCl$_3$, TMS) 1.6–2.9 (m, 6H); 4.2–4.5 (bt, 1H); 7.2 (s, 4H); 8.5 (bs, 1H);

mass spectrum: M$^+$ 253, m/e: 252 (p+2, 10%); 179 (M$^+$-Br); 146 (C=O)

B. 3-Azidohexahydrobenzoazocine-2-one

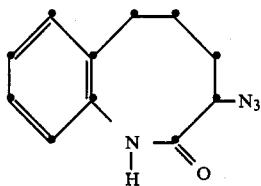

P

To a solution of 10 gm (0.00394 mol) of 3-bromohexahydrobenzoazocine-2-one in 100 ml of dimethylformamide was added 10 gm of sodium azide and the resultant reaction mixture was stirred 12 hours at 60° C.

The DMF was then removed at reduced pressure and the crude product was partitioned between H$_2$O and methylene chloride. The aqueous layer was extracted 3 times with methylene chloride and the combined organic fractions were filtered through MgSO$_4$ and concentrated at reduced pressure. The product was chromatographed (silica, 2:1 ether:hexanes) giving 8 gm of pure azide P.

m.p. 142°–143° C.

TLC (silica, 2:1 ether:hexanes) R$_f$=0.45

An. Calc. for C$_{11}$H$_{12}$N$_4$O.1/4H$_2$O N, 25.36; C, 59.79; H, 5.44 Found N, 25.17; C, 59.37; H, 5.39 NMR (CDCl$_3$, TMS) 1.6–2.9 (m, 6H); 3.4–3.7 (bt, 1H); 7.2 (s, 4H); 8.5 (bs, 1H);

mass spectrum: m/e 188, (M$^+$-N$_2$); 159 (C=O)

C. 3-Azido-1-(t-butoxycarbonylmethyl)-hexahydrobenzoazocine-2-one

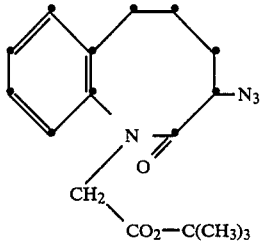

Q

To a suspension of 1.86 gm of sodium hydride (50% suspension, prewashed with hexanes) in 40 ml THF at 0° C. was added dropwise a solution of 8 gm (0.037 mol) of azide lactam and 5.63 ml of t-butyliodo acetate in 40 ml of THF. The reaction was found to be complete upon the completion of the addition. (TLC, silica gel, 2:1 ether:hexanes). The reaction mixture was then quenched by the addition of 20 ml of saturated NH$_4$Cl. The solution was extracted three times with 50 ml portions of ethyl acetate. The combined organic fractions were filtered through MgSO$_4$ and concentrated in vacuo. The crude product was purified by chromatography on silica gel using 2:1 ether:hexanes as eluant. The fractions containing the desired product were combined and concentrated at reduced pressure to give 11 gm of the desired product Q.

m.p. 120°–121° C.

TLC (silica, 2:1 ether:hexanes) R$_f$ =0.75

NMR (CDCl$_3$, TMS) 1.5 (s, 9H); 1.9–3.0 (m, 6H); 3.35–3.6 (dd, 1H); 4.0–4.6 (AB, 2H); 7.2 (s, 4H)

An. Calc. for C$_{14}$H$_{22}$N$_4$O$_3$.½H$_2$O N, 16.50; C, 60.11; H, 6.48 Found N, 16.39; C, 60.29; H, 6.58 mass spectrum: m/e 302, (M+-N$_2$); 257 (M+-OC$_4$H$_9$),

D.

3-Amino-1-(t-butoxycarbonylemthyl)-hexahydrobenzoazocine-2-one

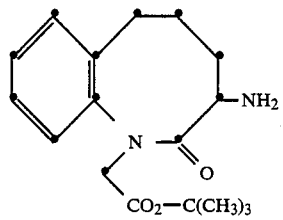

A solution of 9.5 gm (0.0287 mol) of azide lactam Q in 100 ml of absolute ethanol with 900 mg of 10% Pd/C was hydrogenated 12 hours at 40 lbs of hydrogen at room temperature. The reaction mixture was subsequently filtered and the filtrate concentrated in vacuo to give 8.7 gm of amine S. NMR (CDCl$_3$, D$_2$O, TMS) 1.5 (s, 9H); 1.6–2.3 (m, 4H); 2.7–2.9 (t, 3H); 3.2–3.4 (m, 1H); 4.0–4.6 (ABQ, 2H); 7.2 (s, 4H)

E.

1-t-Butoxycarbonylmethyl-3-(1-carboethoxy-3-phenyl-1-propyl)aminohexahydrobenzoazocine-2-one
(Racemate mixture)

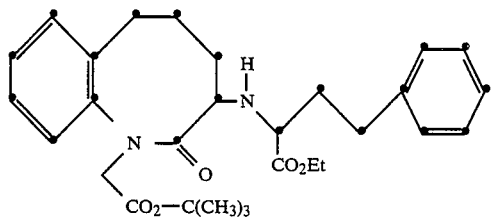

A solution of 2 gm (0.0066 mol) of the 3-amino-1-(t-butoxycarbonylmethyl)-hexahydrobenzoazocine-2-one, 6.7 gm of ethyl-4-phenyl-2-oxobutyrate and 377 ml of acetic acid in 20 ml of ethanol was stirred 1 hour at room temperature. To the stirring reaction mixture was slowly added over a period of 8 hours a solution of 1 gm of sodium cyano borohydride in 20 ml of ethanol. After stirring a further 8 hours the reaction was concentrated at reduced pressure and partitioned between water and ethyl acetate. After extracting twice with ethyl acetate the combined organic layers were filtered through MgSO$_4$ and concentrated in vacuo. The crude reaction mixture was chromatographed (silica, 7:3 hexanes:ethyl acetate) and two diastereomeric racemates of T were isolated.

Racemate diester A 1.7 gm
TLC (7:3 hexanes:ethyl acetate) R$_f$=0.39
NMR (CDCl$_3$, TMS) 1.2 (+, 3H), 1.5 (s, 9H), 1.6–3.2 (m, 13H), 4.1 (Q, 2N), 4.3 (bs, 2H), 6.9–7.2 (m, 9H).

Racemate diester B 1 gm
TLC (7:3 hexanes:ethyl acetate) R$_f$=0.28
NMR (CDCl$_3$, TMS), 1.1 (+, 3H), 1.5 (s, 9H), 1.6–3.2 (m, 13H), 3.9 (Q, 2N), 4.3 (bs, 2H), 7.0–7.2 (two overlapping bs, 9H).

EXAMPLE 9

1-Carboxymethyl-3-(1-carboxy-3-phenyl-1-propyl-)aminohexahydrobenzoazocine-2-one

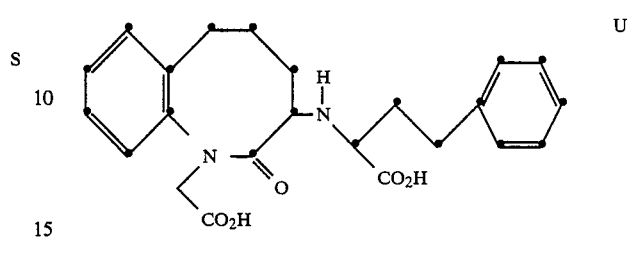

Racemate A

The racemate A diester of Example 8, (1.7 gm) (0.0035 mol) was stirred 1 hour at room temperature with 5 ml of trifluoroacetic acid at which time the reaction mixture was concentrated at reduced pressure. To the crude product in 7 ml of methanol was added 3.5 ml of a 4N solution of sodium hydroxide in water stirring continued overnight at room temperature. The reaction mixture was subsequently applied to a column of Dowex 50 (H+) and eluted first with H$_2$O and then with 5% pyridine. The appropriate pyridine fractions were concentrated giving 600 mg of the diacid U racemate A.

An. Calc. for C$_{23}$H$_{26}$N$_2$O$_5$.½H$_2$O C, 65.80; H, 6.19; N, 6.67 Found C, 66.01; H, 6.32; N, 6.65

NMR (D$_2$O=4.6) 1.5–3.2 (m, 12H), 4.1 (s, 2H), 6.8–7.2 (m, 9H)

Racemate B

The racemate B diester of Example 8 (1 gm, 0.002 mol) was converted to 500 mg of the diacid U by the same procedure as described above.

An. Calc. for C$_{23}$H$_{26}$N$_2$O$_5$.½H$_2$O N, 6.67; C, 65.80; H, 6.19 Found N, 6.62; C, 66.07; H, 6.27

NMR (D$_2$O=4.9) 1.6–3.4 (m, 12H), 4.2 (6s, 2H), 7.2–7.5 (m, 9H)

EXAMPLE 10

1-Carbomethoxymethyl-3-(1-carbomethoxy-3-phenyl-1-propyl)aminohexahydrobenzoazocine-2-one

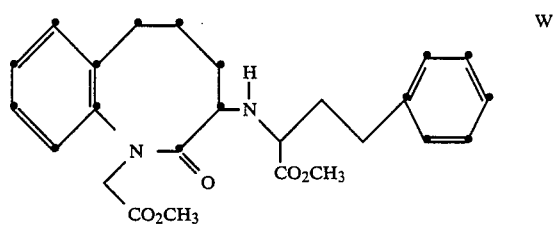

The dimethyl ester W can be prepared from 1-carboxymethyl-3-(1-carboxy-3-phenyl-1-propyl)aminohexahydrobenzoazocine-2-one using a process analogous to that described in Example 5.

EXAMPLE 11

1-Carboxymethyl-3-(1-carboethoxy-3-phenyl-1-propyl-)aminohexahydrobenzoazocine-2-one

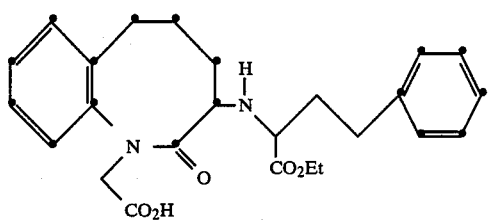   Y

The mono ethyl ester Y can be obtained from the t-butyl/ethyl diester (Racemate B of Example 9) by treatment with trifluoroacetic acid as in the analogous homodihydrocarbostyril Example 6.

EXAMPLE 12

1-Carbobenzyloxymethyl-3-(1-carboxy-3-phenyl-1-propyl)aminohexahydrobenzoazocine-2-one

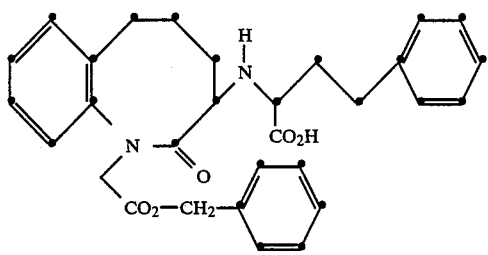   Z

The mono benzyl ester Z may be prepared from 3-amino hexahydrobenzoazocine by a sequence analogous to that described in Example 7.

Examples of the various keto acids and keto esters having the formula:

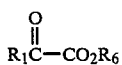

which can be employed in the processes described above to prepare compounds of Formula I are illustrated below in Table I.

TABLE I

Keto Acids and Esters of the Formula $R_1\overset{O}{\underset{\|}{C}}-CO_2R_6$ (a) 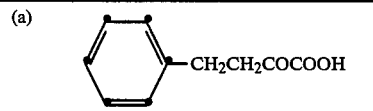

(b) 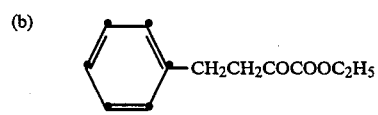

(c) 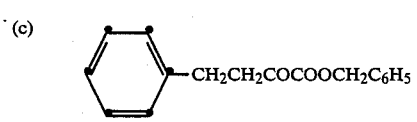

TABLE I-continued

Keto Acids and Esters of the Formula $R_1\overset{O}{\underset{\|}{C}}-CO_2R_6$ (d) Ph—CH₂CH₂CH₂COCOOC₂H₅

(e) Cl—Ph—CH₂COCOOH (f) (indole)—CH₂CH₂COCOOC₂H₅

(g) (thiophene-S)—CH₂CH₂COCOOH (h) (pyridyl)—CH₂CH₂COCOOC₂H₅

(i) (quinolyl)—CH₂CH₂COCOOH (j) HO—Ph—CH₂CH₂COCOOH (k) Cl—Ph—CH₂CH₂COCOOH (l) O₂N—Ph—CH₂CH₂COCOOC₂H₅

(precursor for the corresponding amino compound)

(m) CH₂NH—CBZ—Ph—CH₂CH₂COCOOH (precursor for the corresponding amino compound)

TABLE I-continued
Keto Acids and Esters of the Formula $R_1\underset{\underset{O}{\|}}{C}-CO_2R_6$
(n) 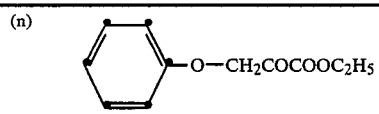
(o) 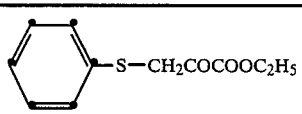
Additional examples of the compounds of Formula I which can be synthesized by the procedures described herein are illustrated by, but not limited to, the compounds illustrated in Table II below:
TABLE II
Additional Examples of Compounds of Formula I
(A) 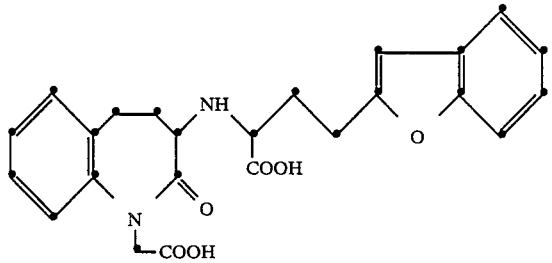
(B) 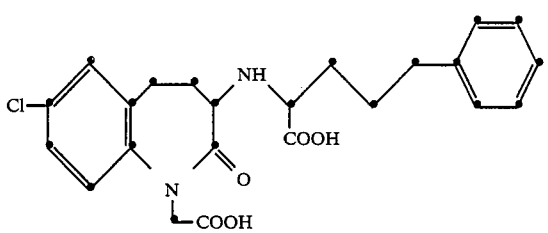
(C) 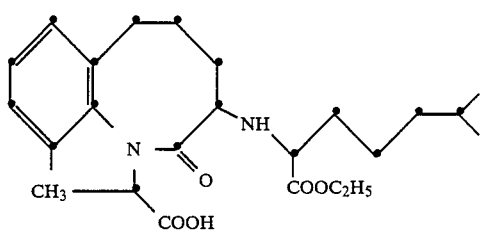
(D) 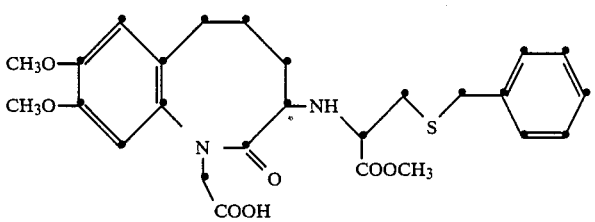
(E) 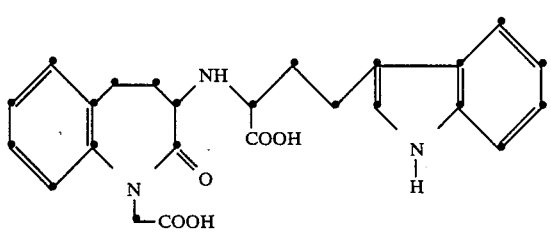

TABLE II-continued
Additional Examples of Compounds of Formula I
(F)
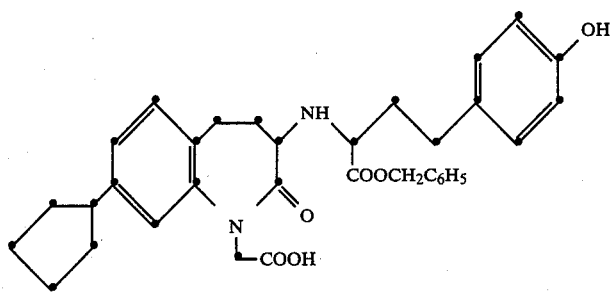
(G)
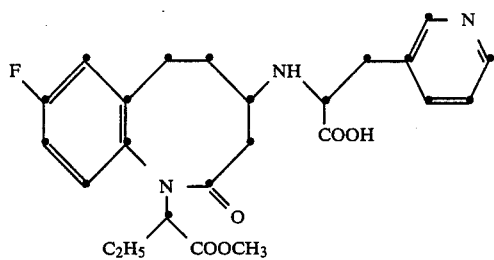
(H)
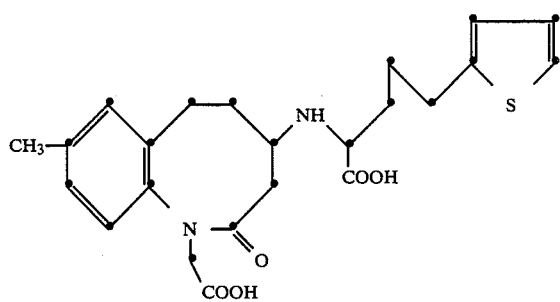
(I)
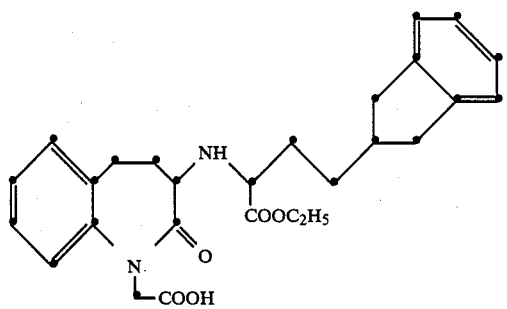
(J)
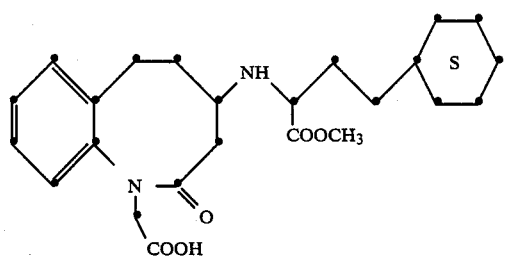
What is claimed is:
1. A compound having the formula:

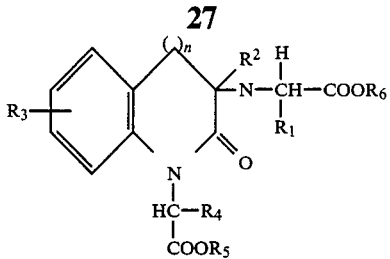

and pharmaceutically acceptable salts thereof wherein n is $R_4$ is hydrogen, lower alkyl, phenyl, phenyl lower alkyl, hydroxy phenyl lower alkyl, hydroxy lower alkyl, amino lower alkyl, acylamino lower alkyl, guanidino lower alkyl, imidazolyl lower alkyl, indolyl lower alkyl, mercapto lower alkyl or lower alkyl thio lower alkyl;

$R_2$ is hydrogen, $R_3$ is H, halo, lower alkyl, cycloalkyl, or loweralkoxy, $R_1$ is hydrogen; hydrocarbon of from 1 to 12 carbon atoms which include branched and unsaturated alkyl groups; cycloalkyl; substituted loweralkyl wherein the substituent can be halo, hydroxy, carboxy, carboxamido, loweralkylthio, loweralkoxy, loweralkoxycarbonyl, lowerarralkoxycarbonyl, amino, loweralkylamino, lowerdialkylamino, acylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di- or trisubstituted by loweralkyl, hydroxy, loweralkoxy, halo, amino, acylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A^1(CH_2)_n$—Q—$(CH_2)_m$ wherein n is 0–2, m is 1–3, $R_A^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, N-$R_B^1$, $CONR_C^1$, $NR_C^1CO$, CH=CH wherein $R_B^1$ is hydrogen, loweralkyl, aryl, aralkyl, loweralkanoyl, or aroyl, and $R_C^1$ is hydrogen, or loweralkyl;

$R_5$ and $R_6$ are independently selected from H, lower alkyl, lower alkenyl, diloweralkylamino, loweralkyl, substituted lower alkyl wherein the substituents are monohydroxy, dihydroxy or acylamino; acylloweralkyl and arloweralkyl; and, the pharmaceutically acceptable salts thereof, wherein in said $R^1$-$R^6$ groups, unless stated otherwise, the alkyl substituents denote straight and branched chain hydrocarbons of $C_1$-$C_{12}$;

loweralkyl denotes alkyl groups of $C_1$ to $C_8$;

alkenyl and alkynyl denote alkyl groups as defined above which are modified so that each contains a carbon to carbon double bond or triple bond, respectively;

cycloalkyl denotes rings composed of 5 to 8 methylene groups, each which may be substituted or unsubstituted with other hydrocarbon substituents;

benzofused cycloalkyl groups denote a cycloalkyl ring of 5 to 8 carbon atoms to which is fused a benzene ring;

bicycloalkyl denotes two cycloalkyl rings of 5 to 8 carbon atoms each joined together in any allowable way;

loweralkoxy substituents denote a loweralkyl group as described above attached through an oxygen bridge;

the aralkyl and heteroaralkyl substituents denote aryl or heteroaryl groups as herein defined attached through a straight or branched chain hydrocarbon of from one to six carbon atoms;

aryl represents phenyl, naphthyl, or biphenyl;

heteroaryl represents any 5- or 6-membered aromatic ring containing from one to three heteroatoms selected from the group consisting of nitrogen, oxygen, and sulfur as well as any bicyclic group in which any of the above heterocyclic rings is fused to another aromatic ring; and acylamino represents loweralkanoylamino and aroylamino.

2. A compound of claim 1 wherein: $R_1$ is loweralkyl, phenyl lower alkyl or amino loweralkyl; $R_3$ is H; $R_4$ is H and $R_5$ and $R_6$ are independently selected from H, lower alkyl or arloweralkyl.

3. A compound of claim 5 wherein $R_1$ is phenylloweralkyl and $R_5$ and $R_6$ are independently selected from H, $CH_3$, $C_2H_5$ or benzyl.

4. A compound of claim 6 wherein $R_1$ is

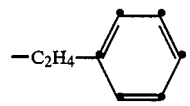

5. A compound of claim 7 wherein $R_5$ is H, $CH_3$ or benzyl and $R_6$ is H, $CH_3$ or ethyl.

6. A compound of claim 7 wherein both $R_5$ and $R_6$ are H or $CH_3$.

7. A pharmaceutical composition for effecting angiotensin converting enzyme inhibition or treating hypertension in humans comprising a pharmaceutically acceptable carrier; and, an angiotensin converting enzyme inhibitive or antihypertensively effective amount of a compound of claim 1.

8. The composition of claim 7 which includes another antihypertensive and/or diuretic selected from the group: amiloride, atenolol, benzofluoromethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazem, fluoroethiazide, atenolol, (+)-4-{3-{-[2-(1-hydroxycyclohexyl)ethyl]-4-oxo-2-thiazolidinyl}propyl}benzoic acid, bumetanide, prazosin, propranolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

9. A method for effecting angiotensin converting enzyme inhibition or treating hypertension which comprises administering to a patient in need of such effectation or treatment an angiotensin converting enzyme inhibitive or antihypertensively effective amount of a compound of claim 1.

10. A process for preparing a compound of claim 1 which comprises coupling of a compound of the formula:

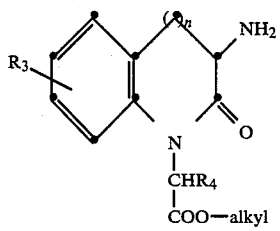

with a compound of the formula:

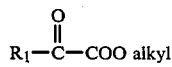

to obtain a compound of claim 1 wherein each of $R_5$ and $R_6$ is alkyl and subsequently hydrolyzing said compound having $R_5$ and $R_6$ alkyl to obtain a claim 1 compound where both $R_5$ and $R_6$ are H and n is 1.

11. A compound having the formula:

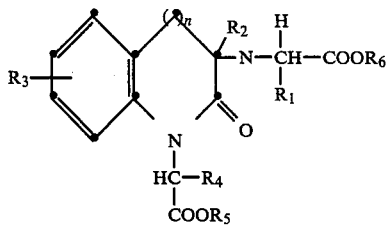

and pharmaceutically acceptable salts thereof wherein n is 1;

$R_4$ is hydrogen, lower alkyl, phenyl, phenyl lower alkyl, hydroxy phenyl lower alkyl, hydroxy lower alkyl, amino lower alkyl, acylamino lower alkyl, guanidino lower alkyl, imidazolyl lower alkyl, indolyl lower alkyl, mercapto lower alkyl or lower alkyl thio lower alkyl;

$R_2$ is hydrogen, $R_3$ is H; halo, lower alkyl, cycloalkyl, or loweralkoxy, $R_1$ is hydrogen; alkyl of from 1 to 12 carbon atoms which include branched and unsaturated alkyl groups; cycloalkyl; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di- or trisubstituted by loweralkyl, hydroxy, loweralkoxy, halo, amino, acylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n—Q—(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, $N-R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R_5$ and $R_6$ are independently selected from H, lower alkyl, lower alkenyl, diloweralkylamino, loweralkyl, substituted lower alkyl wherein the substituents are monohydroxy, dihydroxy or acylamino; acylloweralkyl and arloweralkyl; and, the pharmaceutically acceptable salts thereof, wherein in said $R^1$–$R^6$ groups, unless stated otherwise, the alkyl substituents denote straight and branched chain hydrocarbons of $C_1$–$C_{12}$;

loweralkyl denotes alkyl groups of $C_1$ to $C_8$;

alkenyl and alkynyl denote alkyl groups as defined above which are modified so that each contains a carbon to carbon double bond or triple bond, respectively;

cycloalkyl denotes rings composed of 5 to 8 methylene groups, each which may be substituted or unsubstituted with other hydrocarbon substituents;

benzofused cycloalkyl groups denote a cycloalkyl ring of 5 to 8 carbon atoms to which is fused a benzene ring;

bicycloalkyl denotes two cycloalkyl rings of 5 to 8 carbon atoms each joined together in any allowable way;

loweralkoxy substituents denote a loweralkyl group as described above attached through an oxygen bridge;

the aralkyl and heteroaralkyl substituents denote aryl or heteroaryl groups as herein defined attached through a straight or branched chain hydrocarbon of from one to six carbon atoms;

aryl represents phenyl, naphthyl, or biphenyl;

heteroaryl represents any 5- or 6-membered aromatic ring containing from one to three heteroatoms selected from the group consisting of nitrogen, oxygen, and sulfur as well as any bicyclic group in which any of the above heterocyclic rings is fused to another aromatic ring; and, acylamino represents loweralkanoylamino and aroylamino.

12. Compounds of claim 11 wherein: $R_1$ is loweralkyl, phenyl lower alkyl or amino loweralkyl; $R_3$ is H; $R_4$ is H and $R_5$ and $R_6$ are independently selected from H lower alkyl arloweralkyl.

13. Compounds of claim 12 wherein $R_1$ is phenylloweralkyl and $R_5$ and $R_6$ are independently selected from H, $CH_3$, $C_2H_5$ or benzyl.

14. Compounds of claim 13 wherein $R_1$ is

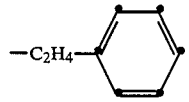

15. Compounds of claim 14 wherein $R_5$ is H, $CH_3$ or benzyl and $R_6$ is H, $CH_3$ or ethyl.

16. Compounds of claim 14 wherein both $R_5$ and $R_6$ are H or $CH_3$.

17. A compound which is: 1-carbomethoxymethyl-3-(1-carboethoxy-3-phenyl-1-propyl)aminodihydrocarbostyril.

18. A compound which is: 1-carboxymethyl-3-(1-carboxy-3-phenyl-1-propyl)dihydro-carbostyril.

* * * * *